United States Patent
Kaasinen et al.

(10) Patent No.: US 8,951,191 B2
(45) Date of Patent: Feb. 10, 2015

(54) APPARATUS FOR DETECTING BODY CONDITION

(75) Inventors: Jussi Kaasinen, Espoo (FI); Matti Karlsson, Viiala (FI)

(73) Assignee: Nokia Corporation, Espoo (FI)

( * ) Notice: Subject to any disclaimer, the term of this patent is extended or adjusted under 35 U.S.C. 154(b) by 1620 days.

(21) Appl. No.: 12/084,513

(22) PCT Filed: Nov. 4, 2005

(86) PCT No.: PCT/FI2005/000474
§ 371 (c)(1),
(2), (4) Date: Mar. 22, 2011

(87) PCT Pub. No.: WO2007/051889
PCT Pub. Date: May 10, 2007

(65) Prior Publication Data
US 2011/0257544 A1    Oct. 20, 2011

(51) Int. Cl.
*A61B 5/00*    (2006.01)
*H04M 11/00*   (2006.01)
*A61B 5/02*    (2006.01)

(52) U.S. Cl.
CPC ........... *A61B 5/0006* (2013.01); *H04M 11/002* (2013.01)
USPC ......................................... 600/301; 600/508

(58) Field of Classification Search
USPC ............ 600/508, 301; 607/30, 32, 59–60, 20; 128/903
See application file for complete search history.

(56) References Cited

U.S. PATENT DOCUMENTS

| | | | | |
|---|---|---|---|---|
| 4,625,733 | A | 12/1986 | Saynajakangas | 128/687 |
| 6,006,132 | A * | 12/1999 | Tacker et al. | 607/5 |
| 6,804,558 | B2 * | 10/2004 | Haller et al. | 607/30 |
| 6,924,773 | B1 * | 8/2005 | Paratte | 343/728 |
| 7,536,211 | B2 * | 5/2009 | Saiki et al. | 455/575.1 |
| 8,260,630 | B2 * | 9/2012 | Brown | 705/2 |
| 2004/0229661 | A1 * | 11/2004 | Shen | 455/575.1 |
| 2005/0064902 | A1 | 3/2005 | Goris et al. | 455/556.1 |
| 2005/0070809 | A1 * | 3/2005 | Acres | 600/508 |

(Continued)

FOREIGN PATENT DOCUMENTS

| | | |
|---|---|---|
| CN | 2549900 Y | 5/2003 |
| CN | 2619581 Y | 6/2004 |

OTHER PUBLICATIONS

The Extended European Search Report for corresponding EP Patent Application No. 05 08 3844, dated Aug. 30, 2011, pp. 1-5.
Chinese Office action for corresponding CN App. No. 200580051630.0 dated Aug. 21, 2009, pp. 1-63.

(Continued)

*Primary Examiner* — Catherine Voorhees
(74) *Attorney, Agent, or Firm* — Ditthavong & Steiner, PC

(57) ABSTRACT

An apparatus for detecting body condition has a communication unit capable of being worn by the body to be detected. The communication unit includes at least one sensor for detecting a signal indicative of the body condition. The apparatus has also a pickup coil of a component of a mobile phone arranged to operate as an inductive antenna for receiving the signal from the communication unit so that said pickup coil is further operable for said component in order to operate the mobile phone. An existing coil in the mobile phone is used for receiving the signal indicative of the body condition from the detector telemetrically. Therefore there is no need to add new components. Existing component can thus be used to detect the signal telemetrically at the mobile phone.

22 Claims, 4 Drawing Sheets

(56) References Cited

U.S. PATENT DOCUMENTS

| | | | |
|---|---|---|---|
| 2005/0171410 A1* | 8/2005 | Hjelt et al. | 600/300 |
| 2005/0197776 A1* | 9/2005 | Makela et al. | 702/4 |
| 2006/0132382 A1* | 6/2006 | Jannard | 345/8 |
| 2008/0215114 A1* | 9/2008 | Stuerzinger et al. | 607/48 |
| 2011/0184259 A1* | 7/2011 | Alarcon et al. | 600/316 |

OTHER PUBLICATIONS

Chinese Office action for corresponding CN App. No. 200580051630.0 dated Jun. 3, 2010, pp. 1-8.

European Office Action for related Patent Application No. 05 803 844.9 dated Sep. 16, 2013, 4 pages.

* cited by examiner

APPARATUS FOR DETECTING BODY CONDITION

TECHNICAL FIELD OF THE INVENTION

The invention concerns an apparatus for detecting body condition. Furthermore the invention concerns a mobile device for illustrating the detected body condition. Yet furthermore the invention concerns a system for monitoring body condition. Yet furthermore the invention concerns the use of such apparatuses.

BACKGROUND ART

Usually in order to measure user's heart rate, for example during sports exercise, a heart rate measurement belt is worn. This belt measures heart's electrical activity. It transmits a trigger signal or the like to a registering device. By counting the time interval between these trigger signals, user's heart rate can be determined and presented. Usually this trigger signal is transmitter in a form of alternating low frequency magnetic field, due to the simplicity of this kind of technology.

In order to implement the alternating low frequency magnetic field registering function to a registering device, a pickup coil is needed. This is of course an additional and extra component meaning extra board space, extra cost and/or increased complexity.

In a known solution dedicated pickup coils have been used to measure the magnetic field signal sent by the measurement belt. Such a known apparatus is disclosed in the closest prior art document U.S. Pat. No. 4,625,733. There is shown a system that describes a procedure, a measurement device, a transmitter and a receiver for telemetric measurement of heartbeat or ECG. The receiver is based on three specific coils therein. The registering coils are designed for accurate results, but as an assembly do not satisfy multipurpose device.

SUMMARY OF THE INVENTION

It is therefore the object of the invention to obtain synergy in the receiver device when detecting body condition for meeting the space and simplicity trend of the hand-held portable devices.

In accordance with a first aspect of the invention there is being provided an apparatus for detecting body condition, comprising a pickup coil of a component of a mobile device arranged to operate as an inductive antenna for receiving a signal indicative of the body condition from a communication unit capable of being worn by the body to be detected, said communication unit including at least one sensor for detecting said signal, and a signal detection system for detecting said signal to be separate from signals from other sources.

In accordance with a second aspect of the invention there is being a mobile device comprising the apparatus.

In accordance with third aspect of the invention there is being provided a system for monitoring body condition, the system comprising a mobile device, comprising:
a pickup coil of a component of said mobile device arranged to operate as an inductive antenna for receiving a signal indicative of the body condition from a communication unit capable of being worn by the body to be detected, said communication unit including at least one sensor for detecting said signal, and a signal detection system for detecting said signal to be separate from signals from other sources, a computer arranged to communicate with said mobile device via a communication network so that the body condition is remotely monitorable via the computer.

In accordance with a fourth aspect of the invention there is being provided a method for detecting body condition, the method comprising detecting a signal indicative of the body condition, sending said signal indicative of the detected body condition, inductively receiving said signal by a pickup coil of a component of a mobile device, detecting said signal so that said signal is identifiable from another signal further operating said component for operating said mobile device, and operating said mobile device by said component.

In the invention the existing coil in the mobile device is used for receiving the signal indicative of the body condition from the detector telemetrically. The signal detection system can detect and identify the signal indicative of the body condition. Furthermore the signal detection system can separate said signal from various other signals. The various other signals are coming from the component and possibly from the pickup coil also. Therefore there is no need to add new components. Existing component can thus be used to detect the signal telemetrically at the mobile device.

Yet further embodiments of the invention have been specified in the dependent claims.

BRIEF DESCRIPTION OF DRAWINGS

The invention will now be described, by way of examples only, with reference to the accompanying drawings, in which.

DESCRIPTION OF FURTHER EMBODIMENTS

Various further embodiments of the invention relate to ways to improve communication between a body condition detecting device and a mobile device. An example of the body condition-detecting device is a heart rate measuring device such as heart rate belt from Polar. Furthermore various further embodiments relate to improving the communication also with a heart rate display device such as Polar wristwatch. It should be noted that the wristwatch can be omitted completely. The mobile device is an example of a hand-held wireless device, which a user can comfortable carry or care. Thus various embodiments of the invention can use the hand-held wireless device. Further examples of the wireless hand-held device are a palm computer or the like, mobile phone or the like etc. Therefore an example of the mobile device can be Nokia™ 5140 mobile phone that is capable of communicating with Polar wristwatch. Various further embodiments could directly use, for example Symbian™ series S60 phones to receive signal from heart rate belt through Java application.

Advantageously the coil of operating mobile device can be used to receive signal directly from the heart rate belt. The coil can, for example, be from a vibramotor of the mobile device or from a loudspeaker of the mobile device.

Furthermore in some further embodiments it is also possible to send information to the wristwatch from the mobile device, like from incoming call a caller id if the device is a mobile phone.

Also some further embodiments use health improvement. Sometimes doctors describe activity prescription. Following those orders can be very difficult. With the further embodiments following the happened activity is simpler and could improve the effect of such prescriptions.

Figure 1:
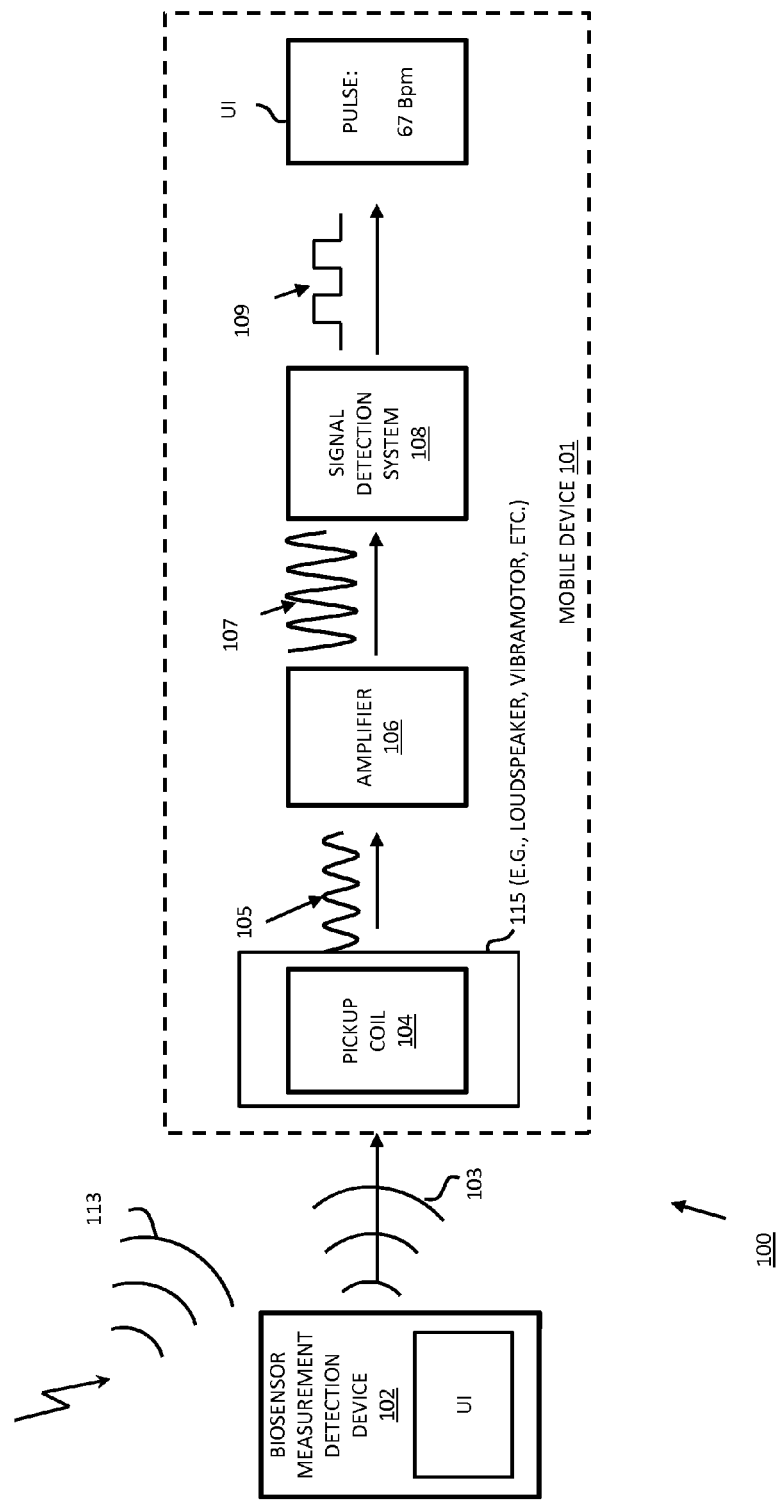
FIG. 1 depicts an apparatus for telemetrically measure body condition with the mobile phone in accordance with a further embodiment of the invention.

Referring now to FIG. 1, there is being depicted an apparatus 100 for telemetrically measure body condition with the mobile device 101 in accordance with a further embodiment of the invention. The apparatus 100 comprises a biosensor measuring device 102. An example of the biosensor measuring device 102 is a heart rate measuring device from Polar including at least the belt and possibly the watch. The biosensor measuring device 102 sends modulated magnetic field 103 containing measured information. The measured information is indicative of the body condition of the user. An example of such a system is Polar hear rate monitoring system.

A coil 104 will pick up the modulated magnetic field 103. The coil 104 is an example of the pickup means of the mobile device 101 receiving inductively the signal. The coil 104 may be referred to as a pickup coil also. Thus one of the existing coils 104 already in the mobile device 101 working as an inductive antenna receives the signal. The coils 104 exist, for example in a component 115 (e.g., a loudspeaker and/or in a vibra motor) of the mobile device 101. It should be noted that other equivalent coil of a component 115 of the mobile device 101 can be used as well as long as it can operate as the inductive antenna. Thus the coil 104 is arranged to operate as a part of the mobile device's conventional functionality. Previously this kind of inductive coil has been implemented by using some extra component in the receiver. In various embodiments the extra component can be omitted. Therefore critical space is saved in the mobile device 101.

From the coil 104 the signal 105 is transferred to an amplifier 106. After the amplification, the signal 107 is transferred to a signal detection system 108. The signal detection system 108 can detect the signal 107 so that the signal can be identified. Thus the signal detection system 108 detects whether the signal 107 is indicative of the detected body condition. Furthermore the signal detection system 108 can detect whether the signal relates to an operation of the component, such as vibrating command signal or a loudspeaker signal etc. Thus the signal detection system 108 is able to categorise the signals it receives from the pick up coil 104.

Referring back to further embodiments of FIG. 1, the signal 107 and also the signal 109 are indicative of the detected body condition. The body condition like the heart rate is presented at user interface UI of the mobile device 101. This way the user can get the information directly to the mobile device 101 for storing and handling.

In various further embodiments if for example the user decides to go jogging, he can have the information directly transported to his mobile device. After the exercise he can send it wirelessly to some other device. Alternatively he can use software in his mobile device to check the quality of the workout. Also the software can contain extra features, which can give him extended information about the exercise during the performance. Thus some embodiments enable customization of the result.

Figure 2:
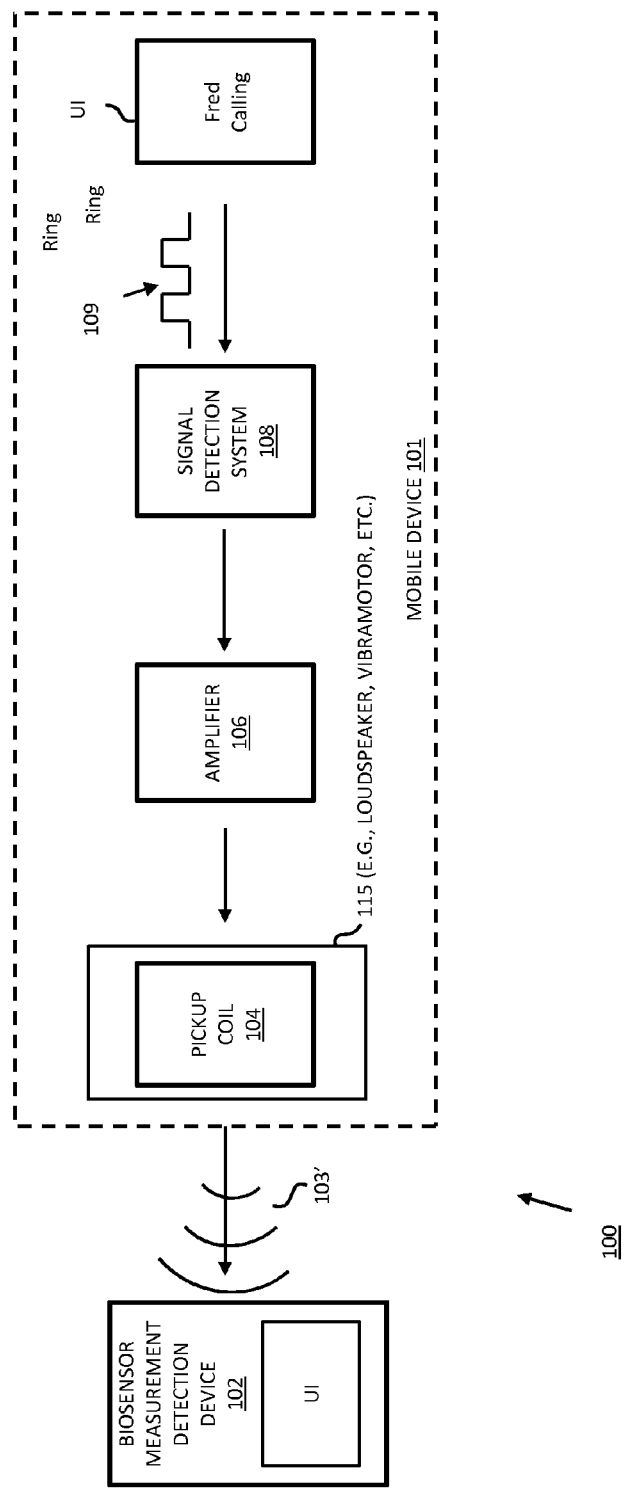
FIG. 2 depicts an apparatus for telemetrically report to back to measurement device in accordance with another further embodiment of the invention.

Referring now to various further embodiments relating to FIG. 2, there is being depicted the apparatus 100 for telemetrically report back to measurement device. In various embodiments of the information with the biosensor system, a body condition display device 110 such as the electronic wristwatch can be used also as external display for the mobile device 101. For example, the user gets a telephone call when jogging. The mobile device 101 sends a message 111 to the watch through signal detection system 108 and through amplifier 106 to the coil 104 acting as the inductive antenna. The coil 104 can be from the vibra motor or from the loudspeaker. The coil 104 acting as the inductive antenna transfers the information, in case of a mobile phone, the caller ID, to the watch via a modulated magnetic field 103'. Advantageously the user does not have to check his mobile device 101 to see who calls. He just has to glance his body condition display device 110 such as the wristwatch. Furthermore other information like SMS or text message can be transferred similarly from the mobile phone 101 to the body condition display device 110.

Figure 3:
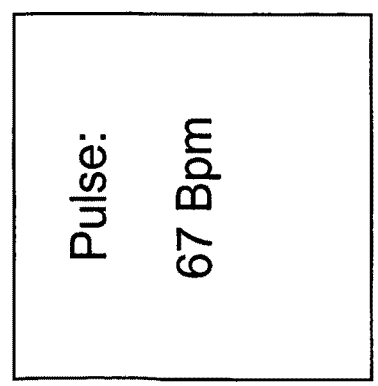
FIG. 3 depicts an example of a user interface in a mobile phone according to another further embodiment of the invention.

FIG. 3 depicts an example of a user interface in a mobile device according to a further embodiment of the invention. The body condition, now the heart beat rate, is shown to the user by his mobile device 101. The body condition detecting device 102 like the heart rate belt detects the body condition. The signal indicative of the condition is inductively transmitted to the mobile device 101 via the coil 104. The mobile device 101 encodes the signal and presents the information of the body condition.

Figure 4:
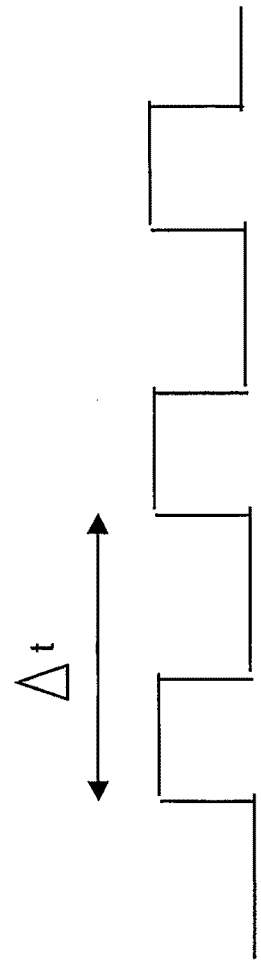
FIG. 4 depicts an example of a signal received from the measuring device in accordance with another further embodiment of the invention.

FIG. 4 depicts an example of a signal received from the measuring device 102 in accordance with a further embodiment of the invention. The desired information is searched from the signal. This is indicated in the FIG. 4 as delta t symbol showing the heart beat rate.

Various Further Implementations

Various further embodiments illustrates that existing coil in the mobile device 101 is used for receiving the trigger signal. An add-on feature to the existing ASIC could amplify this signal. Therefore there is not a need to add new costly components. Furthermore a microcontroller based control is used in some embodiments for converting the measured trigger signal interval into value understandable for user, e.g. heart beats per minute.

Coding and Identifying the Signal

Modern heart rate monitor belts have the possibility to code the sent heart rate signal. This coding can be done using individual code on users mobile device 101. If the device is mobile phone, phone number may be used.

Also the system 108 controlling the coil 104 is able to identify the type of signal it's receiving. Like heart rate signal or signal coming from the mobile device 101 itself. Thus the use of coil 104 can be changed if needed. Like from receiving the heart rate signal to vibrator (which might send additional signal to the wrist watch etc.).

Various Further Appliances

Various embodiments can be used to support workout. At least in some countries there is custom for the doctors, physiotherapist or the like to give exercise prescriptions. This method has its drawbacks, like how to monitor what the patient has done. It is also quite hard for the patient to know what has been the level of exercise, if they have not done any straining physical activity for a long time. Combined with the embodiments the patient needs to have some sort of measuring device, like polar heart rate belt. After that the mobile device (s)he is carrying will do the actual monitoring and data storing.

Further embodiments of the invention apply the sensor technology in wearable devices for more accurate monitoring of target-oriented physical exercise dosage. Furthermore more accurate monitoring of health parameters related to self care of urban diseases such as cardio-vascular diseases, type 2 diabetes, hypertension, obesity, asthma and mental problems. Monitoring is designed in such a way that dosage can be divided into different components, e.g. according to the aerobic performance (basic metabolism, low work load, medium work load and maximum work load). Alternatively, monitoring includes parameters that are commonly used for Evidence Based Medicine (EBM) practises, and parameters that are otherwise considered important and parameters that in the future are identified as essential measures relating to specific diseases. Further embodiments makes it possible to monitor the amount of exercise divided into different components to enable later analysis of achieved response vs. the set target. Alternatively, the pre-defined health parameters such as PEF can be monitored and compared to the EBM practises and targets. The system of the further embodiments also enables iterative target setting based on response follow-up. Setting of targets may be related to preventing or curing a disease, or improving physical condition.

Figure 5:
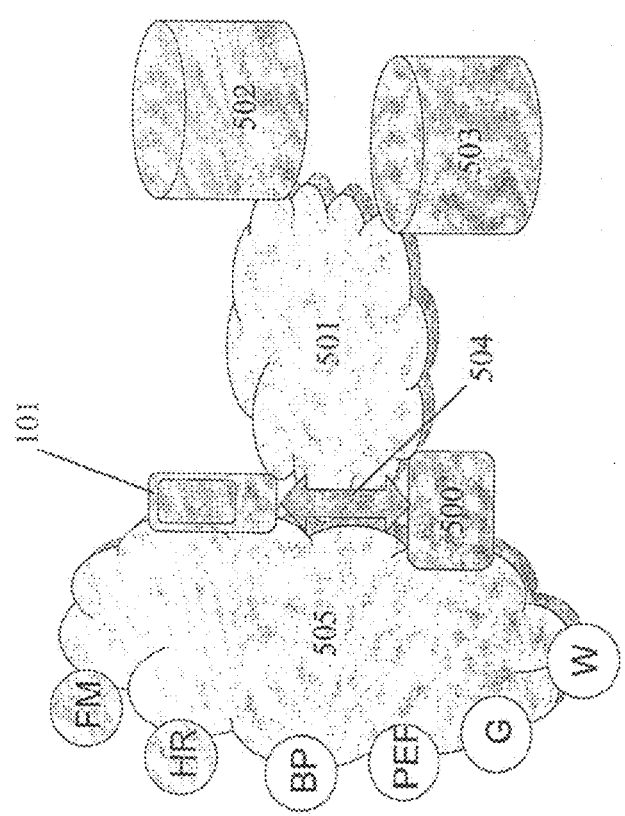
FIG. 5 depicts a system for telemetric mobile monitoring of body condition in accordance with various further embodiments of the invention.

FIG. 5 depicts a system for telemetric mobile monitoring of body condition in accordance with various further embodiment of the invention. The mobile device 101 comprises a sensor link, data logging, target setting, target follow-up and a mobile doctor link to connect the mobile to the doctor database computer. The mobile device 101 is connectable to PC 500 via PC link 504. The PC 500 has EBM guidelines, target setting and target follow-up. Thus the PC 500 communicates with the mobile device 101 for monitoring the body condition of the user. The mobile device 101 has also the sensor link 505 for detecting the body condition(s). An example of the sensor link is the biosensor measuring device 102. An example of the biosensor measuring device 102 can be the heart rate measuring device from Polar including at least the belt and possibly the watch. The HR abbreviation in FIG. 5 denotes a heart rate sensor. FM is a fitness monitor, which means any type of device with inbuilt accelerometers to measure the activity level. This can be a simple pedometer but also more advanced device or even sensor network to measure the body movements e.g. from hands and feet. BP stands for blood pressure. PEF is a peak expiratory flow meter. G denotes glucose measuring device, and W denotes a scale for measuring a weight. Thus the sensor link 505 can detect various different body conditions. Furthermore it should be noted that various kinds of sensor can be coupled with the sensor link 505 to detect various kinds of body conditions. A link 501 couples the PC 500 and/or the mobile device 101 with a healthcare service provider 502 and with a testing service provider 503. In various further embodiments, the link comprises a communication network such as Internet. Furthermore the communication network can be a mobile communication network communicating with the Internet. The healthcare service provider 502 and the testing service provider 503 include EBM guidelines, target setting, target follow-up and a data analysis. Thus the system monitors the body condition of the user even remotely so that a physician can monitor the user (e.g. being a patient). The user can be anywhere under connection to the computer via the link 501 and the physician may be normally situated at the for example hospital.

Various further embodiments have dedicated wearable product including processing platform, necessary software to implement the features described above, inbuilt sensors, connectivity to external sensors, connectivity to the mobile device 101 and PC 500, related analysis software and algorithms, and communications with external service providers 502 and 503. Fitness monitor or similar wearable device to collect signal indicative of the body condition.

An example of the system can be built by using the current Fitness Monitor product and Polar heart rate monitor, both connected to Nokia™ 5140 phone. Furthermore there is provided a phone application, PC software, and the links 501,504 to external service providers.

The system of FIG. 5 can give recommendation of use, e.g. by a doctor about laboratory testing for medical parameters, physical condition, and health status in general. Based on the test result, EBM guidelines and target setting for physical exercise, diet and possible medication can be allocated. Personal and daily monitoring of activity and other defined parameters and comparison to targets with trend analysis can be achieved. Thus even a long term monitoring of health status by healthcare professionals can be comfortable obtained. Furthermore there are cost savings in occupational healthcare. Embodiments of the system enable more accurate control of critical heath factors. An instant gratification (calculated response to actions take can be obtained.

In yet some further embodiments, the pickup coil 104 is further arranged to inductively receive a second signal 113. The second signal 113 can for example be a signal indicative of a thunderbolt or a lightning. The signal detection system 108 further comprises means for identifying the second signal 113. Thereby the apparatus 100 and thus the mobile device can detect the lightning and a thunderstorm.

Ramifications and Scope

Although the description above contains many specifics, these are merely provided to illustrate the invention and should not be constructed as limitations of the invention's scope. It should be also noted that the many specifics can be combined in various ways in a single or multiple embodiments. Thus it will be apparent to those skilled in the art that various modifications and variations can be made in the apparatuses and processes of the present invention without departing from the spirit or scope of the invention.

The invention claimed is:

1. A system for detecting a body condition, comprising:
    a communication unit including at least one sensor, the communication unit being configured to being worn by a user;
    a mobile device comprising,
        a component configured to operate based on one or more signals, the one or more signals including one or more signals related to the body condition and one or more signals unrelated to the body condition, and
        a pickup coil of the component, the pickup coil being configured to operate as an inductive antenna for receiving a first signal indicative of the body condition from the communication unit; and
    a signal detection system configured to separate the received first signal from among the one or more signals unrelated to the body condition.

2. The system according to claim 1, wherein the pickup coil is further configured to operate the component in order to operate the mobile device, and operation of the mobile device creates the one or more unrelated signals from sources unrelated to the body condition.

3. The system according to claim 1, wherein the component comprises a vibramotor of the mobile device and the pickup coil is from the vibramotor.

4. The system according to claim 1, wherein the component comprises a loudspeaker of the mobile device and the pickup coil is from the loudspeaker.

5. The system according to claim 1, wherein the communication unit including the at least one sensor comprises a biosensor measurement detection device.

6. The system according to claim 5, wherein the biosensor measurement detection device is attachable to a wrist of the user.

7. The system according to claim 6, wherein the biosensor measurement detection device comprises a wrist watch.

8. The system according to claim 5, wherein the biosensor measurement detection device is attachable to a chest of the user.

9. The system according to claim 8, wherein the biosensor measurement detection device comprises a belt.

10. The system according to claim 5, wherein the biosensor measurement detection device includes a user interface configured to display information relating to the mobile device, the information being received from the mobile device.

11. The system according to claim 10, wherein the information comprises caller identification information.

12. The system according to claim 1, wherein the first signal is transmitted inductively between the communication unit and the pickup coil.

13. The system according to claim 1, wherein the system further comprises an amplifier for amplifying the received first signal.

14. The system according to claim 1, wherein the system further comprises signal detection means for processing the first signal so that the body condition is indicated.

15. The system according to claim 1, wherein the system further comprises a user interface of the mobile device for presenting the detected body condition.

16. The system according to claim 1, wherein the pickup coil is further configured to inductively receive a second signal indicative of a lightning or a thunderbolt and the signal detection system is further configured to detect the received second signal from among the one or more signals used for operating the component.

17. A mobile device for detecting a body condition, comprising:
   a component configured to operate based on one or more signals, the one or more signals including one or more signals related to the body condition and one or more signals unrelated to the body condition;
   a pickup coil of the component, the pickup coil being configured to operate as an inductive antenna for receiving a first signal indicative of the body condition; and
   a signal detection system configured to separate the first signal indicative of the body condition from among the one or more signals unrelated to the body condition after the first signal has been received at the pickup coil.

18. A system for monitoring a body condition, the system comprising:
   a biosensor measurement device configured to being worn by a user, the biosensor measurement device comprising a communication unit, the communication unit including at least one sensor;
   a mobile device, comprising,
      a component configured to operate based on one or more signals, the one or more signals including one or more signals related to the body condition and one or more signals unrelated to the body condition,
      a pickup coil of the component, the pickup coil being configured to operate as an inductive antenna for receiving a first signal indicative of the body condition from the biosensor measurement detection device, and
      a signal detection system configured to separate the first signal from among the one or more signals after the first signal unrelated to the body condition has been received at the pickup coil; and
   a computer arranged to communicate with the mobile device via a communication network so that the body condition is remotely monitorable via the computer.

19. A system according to claim 18, wherein the computer sends instructions in response to the detected body condition, which detected body condition is communicated to the computer.

20. A system according to claim 18, wherein the computer remotely arranges the monitoring of the body condition by a person operating the computer.

21. A system according to claim 20, wherein the computer receives the detected body condition, presents the detected body condition, and sends the instructions to the mobile phone.

22. A method for detecting a body condition, the method comprising:
   inductively receiving one or more signal including a first signal indicative of the body condition at a pickup coil of a component of a mobile device; and
   separating the first signal indicative of the body condition from among the one or more signals, the one or more signals including one or more signals related to the body condition and one or more signals unrelated to the body condition.

* * * * *